United States Patent [19]

Boyd

[11] Patent Number: 4,503,149
[45] Date of Patent: Mar. 5, 1985

[54] METHOD OF MICROBIAL ASSAY

[75] Inventor: Phil A. Boyd, Ponca City, Okla.

[73] Assignee: Conoco Inc., Ponca City, Okla.

[21] Appl. No.: 501,480

[22] Filed: Jun. 6, 1983

[51] Int. Cl.$^3$ .................. C12Q 1/06; C12Q 1/08; G01N 21/33

[52] U.S. Cl. .................. 435/39; 250/373; 250/461.2; 435/6; 435/40; 435/808; 436/63; 436/94; 436/164; 436/177

[58] Field of Search .................. 250/372, 373, 459.1, 250/461.1, 461.2; 435/6, 8, 39, 40, 291, 808; 436/63, 86, 94, 164, 175, 177

[56] References Cited

U.S. PATENT DOCUMENTS

| | | | |
|---|---|---|---|
| 3,616,253 | 10/1971 | D'Eustachio | 435/39 X |
| 3,745,090 | 7/1973 | Chappelle et al. | 435/39 X |
| 3,864,212 | 2/1975 | Berkhan | 435/6 |
| 3,928,139 | 12/1975 | Dorn | 435/39 X |
| 3,971,703 | 7/1976 | Picciolo et al. | 195/103.5 |
| 4,154,821 | 5/1979 | Drouet et al. | 424/177 |
| 4,174,772 | 11/1979 | Neuss et al. | 435/32 |

FOREIGN PATENT DOCUMENTS 924103  4/1982  U.S.S.R. .................. 435/6

OTHER PUBLICATIONS

Cherry, Plant Physiology, vol. 37, No. 5, pp. 670–678 (1962).

*Primary Examiner*—Arnold Turk
*Assistant Examiner*—Robert J. Hill, Jr.
*Attorney, Agent, or Firm*—A. Joe Reinert

[57] ABSTRACT

A process for detecting the population count of microorganisms in an aqueous medium by means of ultraviolet spectrophotometry. The specimen is first filtered and the resulting filtrate then centrifuged to concentrate the microbial cells in a pellet layer. The microbial cells are then redispersed in an aqueous solution having a volume less than the volume of the original specimen and the absorption of ultraviolet light by the redispersed solution at wavelengths within the range of 260–280 nanometers is measured. The concentrated microbial cells may be lysed in order to release nucleic acid and protein components from the cellular wall structure.

5 Claims, No Drawings

METHOD OF MICROBIAL ASSAY

DESCRIPTION

1. Technical Field

This invention relates to the determination of the population count of microorganisms in aqueous media and, more particularly, to such determinations based upon absorption of ultraviolet light by the nucleic acid and protein components of microorganisms

2. Background of the Invention

There are various applications in which it is desirable to obtain a gross indication of the quantity of microorganisms present in an aqueous fluid. One application is in the monitoring of municipal water supplies. Another is in the monitoring of injection waters employed in oil field operations such as in salt water disposal or as displacing media in enhanced oil recovery operations. In such oil field operations, the presence of bacteria or other acellular or unicellular microorganisms such as microalgae or protozoa may result in damage to the subterranean formation into which the water is injected.

In such applications, bacterial (or other microbial) populations of only a few thousand per milliliter may ultimately result in damage to the formation. Thus, it is desirable to detect bacteria in only modest contamination levels and also to attain a qualitative bacterial assay in order to arrive at a proper treatment procedure. One commonly employed technique for bacterial assay involves the serial dilution procedure. With this technique, a unit volume of sample water is obtained and injected into a specified volume of an aqueous culture medium. Typically, 1 milliliter of sample water is injected into 9 milliliters of nutrient solution to provide a culture of 10 milliliters. After agitation to provide a homogenous mixture, 1 milliliter of this medium is withdrawn and injected into 9 milliliters of a second nutrient solution. This procedure is continued to obtain the desired number of dilutions, typically from 4 to 6. The culture solutions are then incubated at a standard temperature for a period of several days or weeks after which they are examined for evidence of growth in order to arrive at an indication of the population of the original sample. While the serial dilution technique is capable of detecting low bacteria populations, e.g., a few hundred per milliliter, it may take several weeks to complete. If during this period, water injection is carried out, considerable formation damage, e.g., plugging or irreversible contamination, could result due to the presence of only moderate population levels of bacteria or other microorganisms.

Another bacterial assay technique is based upon the bioluminescent reaction of bacterial adenosine triphosphate (ATP) with a measurement of the emitted light energy providing a qualitative indication of the bacteria population. As disclosed, for example, in U.S. Pat. No. 3,971,703 to Piccolo et al., a sample containing non-bacterial materials is treated to rupture the non-bacterial cells and release the nonbacterial ATP. The solution may be concentrated by centrifuging before or after this rupturing step. After eliminating the nonbacterial ATP, the solution is centrifuged and the bacterial cells are lysed or ruptured. The bacterial ATP solution is mixed with luciferin and luciferase, an enzyme which catalyzes the bioluminescent reaction. The light emitted is measured by a photomultiplier tube in order to provide a quantitative determination of the bacterial ATP and, thus, the bacteria cells present in the original sample.

This technique is limited by the sensitivity with which the light reaction can be measured. Typically, bacterial populations less than 5000/ml cannot be measured because of the small amount of light produced in the bioluminescent reaction. Also, enzyme inactivation may occur because of factors such as pH changes or the presence of heavy metals.

DISCLOSURE OF THE INVENTION

In accordance with the present invention, there is provided a new and improved microbial bioassay technique in which the microorganism population count is determined by ultraviolet spectrophotometry. In carrying out the invention, the specimen under investigation is filtered to remove multi-cellular components. The resulting filtrate containing the microbial cells is recovered and centrifuged to concentrate the microbial cells in a pellet layer. The pellet layer is removed from the supernatant fluid and redispersed in a aqueous solution having a volume less than the volume of the original specimen in order to provide an increased cell concentration. This solution is then subjected to ultraviolet spectrophotometry in order to measure the absorption of ultraviolet light at wavelengths within the range of 260–280 nanometers.

In a preferred embodiment of the invention, the concentrated solution is subject to a lysing procedure in order to rupture the microbial cells and release nucleic acid and protein components from the cellular wall structure. The solution is then subjected to the ultraviolet spectrophotometric measurement. In a further aspect of the invention the nucleic acid and protein components are separated from the other cellular components prior to the absorption measurement.

BEST MODES FOR CARRYING OUT THE INVENTION

As is known to those skilled in the art, proteins and nucleic acids are universally found in all biological systems. They are present in bacteria and other microbial cells at fairly constant levels throughout species diversification. Both the proteins and nucleic acids display a strong absorption of ultraviolet light in the spectral range of 260–280 nanometers (nm). In the present invention, these relationships are utilized to advantage to provide a microbial assay technique for making a quantitative determination of cell population which is responsive to low population levels and which can be carried out rapidly and inexpensively. In the first step of the invention, a specimen is obtained from the aqueous fluid under investigation and filtered through a millipore filter in order to separate the microbial cells from the higher organisms and other multi-cellular debris present in the specimen. For example, the specimen may be filtered through a two micron filter so that the multi-cellular components are filtered out in the filter cake leaving the microbial cells in the filtrate.

The filtrate is composed primarily of bacteria and other acellular or unicellular organisms and is substantially free of higher organisms which, because of their nucleic acid and protein content, would exhibit absorption within the ultraviolet spectrum of interest. Subsequent to the filtering step, the specimen is centrifuged to concentrate the microbial cells in the bottom pellet layer. The centrifuging step may be carried out under any suitable conditions of force and time. Typically, the filtrate will be centrifuged for a period of about five to thirty minutes, at a force of 500 to 1000 g's. For example, in most cases, it will be suitable to centrifuge the filtrate at 600 g's. for ten minutes.

Subsequent to the centrifuging step, the supernatant fluid is withdrawn from the microbial pellet layer and the microbial cells then redispersed in an aqueous solution having a volume less than the volume of the original specimen in order to increase the cell concentration. As a practical matter, the redispersing solution should have a volume of about ¼ or less than the volume of the original specimen in order to provide at least a four-fold increase of bacteria concentration present in the original specimen. Typically, the ratio of the volume of the redispersing specimen solution to the volume of the original specimen will range from about ¼ to 1/20. The redispersing solution may be any suitable aqueous solution which is optically clear. For example, the bacterial pellet may be dispersed in an aqueous solution having a salinity due to the presence of inorganic salts (normally sodium chloride) of about 0.9%.

The redispersed solution may now be subjected to ultraviolet spectrophotometry in order to measure the absorption of ultraviolet light within the wavelength spectrum of 260–280 nanometers. The absorption measurements may be carried out at selected frequencies within this range or across the entire band width. In general, absorption by the nucleic acids predominates near the 260 nanometer wavelength and absorption by the proteins predominates near the 280 nanometer region, and it usually will be preferred to carry out the measurements across a substantial portion of the 260–280 nm range in order that the measurements reflect substantial absorption by both types of components. Regardless of the wavelengths at which the ultraviolet absorption is measured, it is, of course, necessary that the absorption measurements be correlated with calibration measurements carried out on known bacteria concentrations under the same conditions. Thus, if the absorption measurements are to be carried out across the 260–280 nanometer band width, for example, these must be compared with calibration mesurements similarly carried out across the 260–280 nanometer band width.

The absorption of ultraviolet light may be measured by any suitable technique. Normally, it will be desirable to use a double-beam ultraviolet spectrophotometer in which ultraviolet light from the same source or from matched sources is passed alternately through the sample under investigation and through a reference sample, i.e., an aqueous fluid identical to the dispersing fluid but free of microbial content. The energy levels of the two beams can then be analyzed in accordance with the Beer-Lambert relationship and the resulting absorption value compared with the appropriate calibration measurements. Ultraviolet spectroscopy is well known to those skilled in the art and, accordingly, will not be discussed further.

While the ultraviolet absorption measurements can be carried out directly on the redispersed bacterial solution, as noted above, in accordance with a preferred embodiment of the invention, the microbial cells are first lysed in order to rupture the cell walls in order to release the nucleic acid and protein components from the cellular wall structure. The lysing step may be carried out using any suitable procedure as will be understood by those skilled in the art. Thus, lysing may be accomplished enzymatically with various enzymes, physically with acoustic or electromagnetic radiation, chemically through the use of surface active agents or acids, or mechanically with homogenous mixing techniques. By way of example, lysozyme may be mixed with the redispersed bacterial solution and the solution maintained at a moderately elevated temperature for a period of time to allow the lysing to take place. For example, lysozyme may be added to the microbial solution to provide a lysozyme concentration of about 25 parts per million and the solution allowed to incubate for 30–60 minutes at 37° C. Alternatively, the redispersed microbial solution may be subjected to ultrasonic lysing by exposing the solution to sound at a frequency of about 50 to 100 KHz at room temperature for a short period of time, e.g., an hour or less. Mechanical lysing may be carried out simply by mechanically stressing the microbial solution in a tissue homogenizer for a period of 10–60 minutes. For a further description of various well known lysing techniques, reference may be made to U.S. Pat. No. 4,154,821 to Drouet et al. Regardless of the lysing technique used, it will again be recognized that the ultraviolet absorption measurements obtained should be correlated with calibration measurements obtained under similar conditions in order to arrive at an accurate quantitive analysis of the microbial cell population.

It is preferred, subsequent to the lysing step, to subject the lysate to a further separation step prior to the ultraviolet absorption spectroscopy procedure. The separation step is carried out in order to effect a separation of the nucleic acid and protein components from the cellular wall structure. While such separation can be accomplished by means of chromatographic-type separation technique, it is preferred to centrifuge the lysate in order to isolate the protein and nucleic acid components in the lower pellet layer. In order to clearly and sharply isolate the nucleic acid and protein components from the wall debris, it is preferred to carry out the centrifuging step in a density graded medium. For example, the lysate may be added to the top of an aqueous sucrose solution in which the density is graded from a low-density upper layer of 20% sucrose to a high-density lower layer of 60% sucrose in increments of 10% sucrose. The resulting suspension can then be centrifuged for a period of about 30 minutes at about 1000 g's in order to concentrate the nucleic acid and protein components in the lower high-density layer. At the conclusion of the separation step, the nucleic acid and protein components can then be resuspended in a suitable aqueous medium, e.g., a saline solution as described previously, and this sample then subjected to the ultraviolet absorption measurements as noted above.

Having described specific embodiments of the present invention, it will be understood that certain modifications thereof may be suggested to those skilled in the art and it is intended to cover all such modifications as fall within the scope of the appended claims.

What is claimed is:

1. A method for determining the quantity of microorganisms in an aqueous specimen which contains microorganisms and multicellular organisms, the steps comprising:
   (a) filtering said specimen to remove the multicellular organisms therefrom and recovering the filtrate containing the microorganisms;
   (b) centrifuging said filtrate to concentrate the microorganisms in a pellet layer and removing supernatant fluid from said pellet layer;

(c) redispersing said pellet of the microorganisms in an aqueous solution having a volume less than the volume of said original specimen to provide an increased concentration of the microorganisms; and (d) measuring the absorption of ultraviolet light by said aqueous solution at a wave length within the range of 260–280 nanometers, said absorption being directly proportional to the quantity of the microorganisms.

2. A method of determining the quantity of microorganisms in an aqueous specimen containing microorganisms and multicellular organisms, comprising:

(a) filtering said specimen to remove the multicellular organisms therefrom and recovering the filtrate containing the microorganisms;

(b) centrifuging said filtrate to concentrate the microorganisms in a pellet layer and removing supernatant fluid from said pellet layer;

(c) redispersing said pellet of microorganisms in an aqueous solution having a volume less than the volume of said original specimen to provide an increased concentration of the microorganisms;

(d) lysing the microorganisms in said solution to rupture cells and release nucleic acid and protein components from the cellular wall structure; and (e) measuring the absorption of ultraviolet light by said solution at a wavelength within the range of 260–280 nanometers said absorption being directly proportional to the quantity of the microorganisms.

3. The method of claim 2 further comprising the step of separating the nucleic acid and protein components from the cellular wall structure of the microorganisms and carrying out absorption measurement of step (e) on said nucleic acid and protein components.

4. The method of claim 3 wherein said separation is effected by centrifuging the lysed solution to concentrate the nucleic acid and protein components in a pellet layer.

5. The method of claim 4 wherein centrifuging of said lysed solutions is carried out in a density graduated medium.

* * * * *